United States Patent [19]

Gray et al.

[11] 4,052,286
[45] Oct. 4, 1977

[54] SOLID SENSOR ELECTRODE

[75] Inventors: Don N. Gray, Sylvania, Ohio; George G. Guilbault, New Orleans, La.

[73] Assignee: Owens-Illinois Inc., Toledo, Ohio

[21] Appl. No.: 328,360

[22] Filed: Jan. 31, 1973

[51] Int. Cl.² ........................................... G01N 27/46
[52] U.S. Cl. ................................. 204/195 R; 204/292; 427/125; 65/18
[58] Field of Search .......... 204/195 M, 195 G, 195 S, 204/280, 290 R, 290 F, 291–293

[56] References Cited

U.S. PATENT DOCUMENTS 3,700,577  10/1972  Grauer ............................ 204/195G

FOREIGN PATENT DOCUMENTS 1,081,545  8/1967  United Kingdom ............ 204/195 S Primary Examiner—T. Tung
Attorney, Agent, or Firm—David H. Wilson, Jr.; Richard D. Heberling

[57] ABSTRACT

A noble metal-glass composite is screen printed on an inert substrate such as a low alkali glass and fired to provide a solid sensor electrode.

9 Claims, 7 Drawing Figures

CYCLIC POLAROGRAMS OF 1.0 × 10⁻³ M K₄Fe(CN)₆ IN 0.1 M PHOSPHATE BUFFER pH 6.0

A. PLATINUM INLAY ELECTRODE

B. GOLD SOLID SENSOR ELECTRODE

SOLID SENSOR ELECTRODE

BACKGROUND OF THE INVENTION

Noble metals have been used as electrodes which find application in potentiometric, amperometric and various other electrochemical procedures. Platinum wire electrodes in particular have achieved wide usage. More recently platinum inlay, silver billet and gold button electrodes have partially replaced the more conventional wire electrodes.

The noble metal electrodes heretofore available, however, have been relatively expensive. In addition such electrodes are not particularly durable, especially when in the form of fine wires. Another disadvantage of noble metal electrodes is that they are easily poisoned due to absorption of organic and other impurities upon the noble metal surface.

It is accordingly an object of this invention to provide an improved type of noble metal electrode.

Another object of this invention is to provide a less expensive electrode which can be used instead of the noble metal electrodes currently in use.

Another object of this invention is to provide an electrode which is more durable than present noble metal electrodes. an electrode which is not easily poisoned.

Other objects and advantages of this invention will become apparent from the following detailed disclosure and description.

SUMMARY OF THE INVENTION

A solid sensor electrode which has all of the advantages of the noble metal electrodes in use today and which overcomes the disadvantages thereof can be fabricated by affixing a composite of a noble metal and glass to an inert substrate. This is readily accomplished by screen printing a mixture of a noble metal powder and glass in a fugitive vehicle upon the substrate and firing at an elevated temperature to mature the noble metal-glass composite by removing the fugitive vehicle and fusing the glass which acts as a binder.

The electrodes of this invention are characterized by a high degree of durability and resistance to poisoning. They are readily fabricated and can be furnished in any desired configuration. These electrodes can be used in any application where a noble metal electrode would be useful and, because of their versatility, in many other applications where the previously available noble metal electrodes would not be suitable.

DESCRIPTION OF THE PREFERRED EMBODIMENTS

Figure 1:
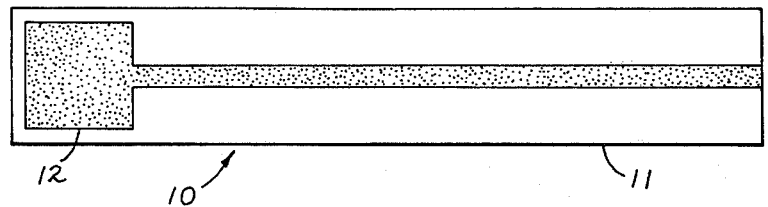
FIG. 1 is an elevational view of one embodiment of the solid sensor electrode of this invention. The numeral 10 represents a solid sensor electrode which comprises an inert substrate 11 having imprinted thereon a noble metal-glass composite 12.

The inert substrate to which is affixed the noble metal-glass composite, to be hereinafter described, is preferably formed of glass or a suitable plastic material, but other substrate materials may be used if desired.

If glass is used as the substrate material it is desirable that the glass be a chemically pure, low alkali glass because it is necessary for the solid sensor electrode including the substrate to remain in various solutions for extended periods of time and it is well known that alkalis present in glass are subject to diffusion and leaching out. In addition glasses containing substantial proportions of alkali exhibit poor adhesion.

Low alkali glasses are well known and generally contain alkaline earth metal oxides instead of those of the alkali metals. A typical formulation, for example contains 44.9% silica ($SiO_2$), 19.0% alumina ($Al_2O_3$), 15.1% magnesium oxide (MgO) and 21.0% calcium oxide (CaO) by weight and is a chemically durable, hard glass.

Other low alkali glass compositions, a variety of which are known, may be used as well.

Plastic materials suitable for use as substrates should be chemically inert, sufficiently thermoplastic to enable the noble metal-glass composite to be affixed thereto by treatment at elevated temperatures and yet resistant to deformation at slightly elevated temperatures. Plastics which are suitable for this purpose in general have high heat distortion temperatures and include, for example, the polyimides and polyimide/amides.

Other materials which can be used as the substrate include alumina and other refractory materials, such as ceramics having the requisite chemical durability and heat stability.

The composite of noble metal and glass which is to be affixed to the inert substrate can be prepared using a nobel metal powder such as gold, platinum, palladium or silver or a mixtue of two or more of these metals together with a pure glass binder of low alkali content. Such binder might include oxides of various metals such as bismuth, cadmium, aluminum, zinc and lead or various non-metal oxides including silicon and boron oxides, for example. Glass binder formulations can be provided from a wide mixture of materials depending upon the particular properties desired for the noble metal-glass composite. Secondary considerations governing the choice of binder include the facility with which the composite can be printed upon the substrate and the temperatures at which the substrate having the noble metal-glass composite imprinted thereupon is to be fired.

In general the noble metal should be present in the matured composite in a percentage of about from 50% to 99% by weight of the composite with the glass binder providing the remainder of the composite composition.

The noble metal powder and powdered glass binder, both in finely divided form, are mixed in a suitable fugitive vehicle to form a paste and printed upon the substrate using standard screen printing techniques. The use of a fugitive vehicle facilitates the application of the mixture of noble metal power and glass binder to the substrate. Suitable vehicles will be chemically inert and combustible at temperatures at which the printed substrate is to be fired. One such useful vehicle contains 15% by weight of ethyl cellulose and 85% by weight of a mixture of 67% by volume of butylcarboxyl acetate and 33% by volume of isoamyl salicylate. Other vehicles such as poly-(alpha-methylstyrene) and other pyrolyzable polymers can also be used. In general any vehicle having the properties listed above such as those used in thick film printing are satisfactory for use in fabricating the solid sensor electrodes of this invention.

The fugitive vehicle is removed by firing at a temperature which is sufficient to cause fusing of the printed composite to the substrate. In general the temperature depends upon the particular choice of substrate with temperatures above about 800° C. being required for maturing the printed substrate. A temperature of about from 800° C. to 1100° C. can be used for this purpose. A temperature of about 880° C. is especially preferred. Maturing takes place in about from 20 minutes to 2 hours.

The substrate itself and the application of the noble metal-glass composite thereto may be in any desired geometrical form depending upon the use to which the finished electrode is to be put.

Upon maturing, the resulting construction is ready to be used as an electrode by making the appropriate electrical connections.

The formulation and use of the electrodes of this invention will be described in the following detailed examples which are intended to illustrate the instant invention without placing any unnecessary limitations thereon. All parts and percentages are by weight unless otherwise noted.

EXAMPLE 1

The substrate used was a chemically pure, low alkali glass having the composition shown in Table 1.

TABLE I

|  | % |
|---|---|
| $SiO_2$ | 44.9 |
| $Al_2O_3$ | 19.0 |
| MgO | 15.1 |
| CaO | 21.0 |

Plates 4 inches long, ½ inch wide and ⅛ inch thick were cut from this glass.

On to these plates was screened a paste formed from the ingredients shown in Table 2 and a vehicle consisting of 15% ethyl cellulose and 85% of a mixture of 67% by volume of butylcarboxyl acetate and 33% by volume of isoamyl salicylate.

TABLE 2

|  | % |
|---|---|
| Ag | 54.6 |
| Pd | 31.4 |
| $Bi_2O_3$ | 11.0 |
| CdO | 2.0 |
| $SiO_2$ | 1.0 |

The screen printed substrate was then fired in air at a temperature of 880° C. for a period of 1 hour.

EXAMPLE 2

The procedure of Example 1 was followed except that the noble metal-glass composite was prepared by mixing 90 parts of silver powder, 6.7 parts of bismuth oxide and 3.3 parts of powdered glass having the composition shown in Table 3.

TABLE 3

|  | % |
|---|---|
| PbO | 60.0 |
| $SiO_2$ | 17.6 |
| $B_2O_3$ | 16.0 |
| $Al_2O_3$ | 2.1 |
| CdO | 4.3 |

EXAMPLE 3

The procedure of Example 1 was followed except that the noble metal-glass composite was prepared by mixing 96 parts of gold powder and 4 parts of powdered glass having the composition shown in Table 4.

TABLE 4

|  | % |
|---|---|
| PbO | 57.0 |
| ZnO | 21.0 |
| $B_2O_3$ | 22.0 |

Example 4

The procedure of Example 1 was followed except that the noble metal-glass composite was prepared by mixing 96 parts of platinum powder and 4 parts of powdered glass having the composition shown in Table 4.

EXAMPLE 5

The procedure of Example 1 was followed except that the noble metal-glass composite was prepared by mixing the ingredients shown in Table 5.

TABLE 5

|  | % |
|---|---|
| Au | 54.6 |
| Pd | 31.4 |
| $Bi_2O_3$ | 11.0 |
| CdO | 2.0 |
| $SiO_2$ | 1.0 |

EXAMPLE 6

The procedure of Example 1 was followed except that the substrate used was alumina and the screen printed substrate was fired at a temperature of 1100° C. for a period of 2 hours.

EXAMPLE 7

Figure 2:
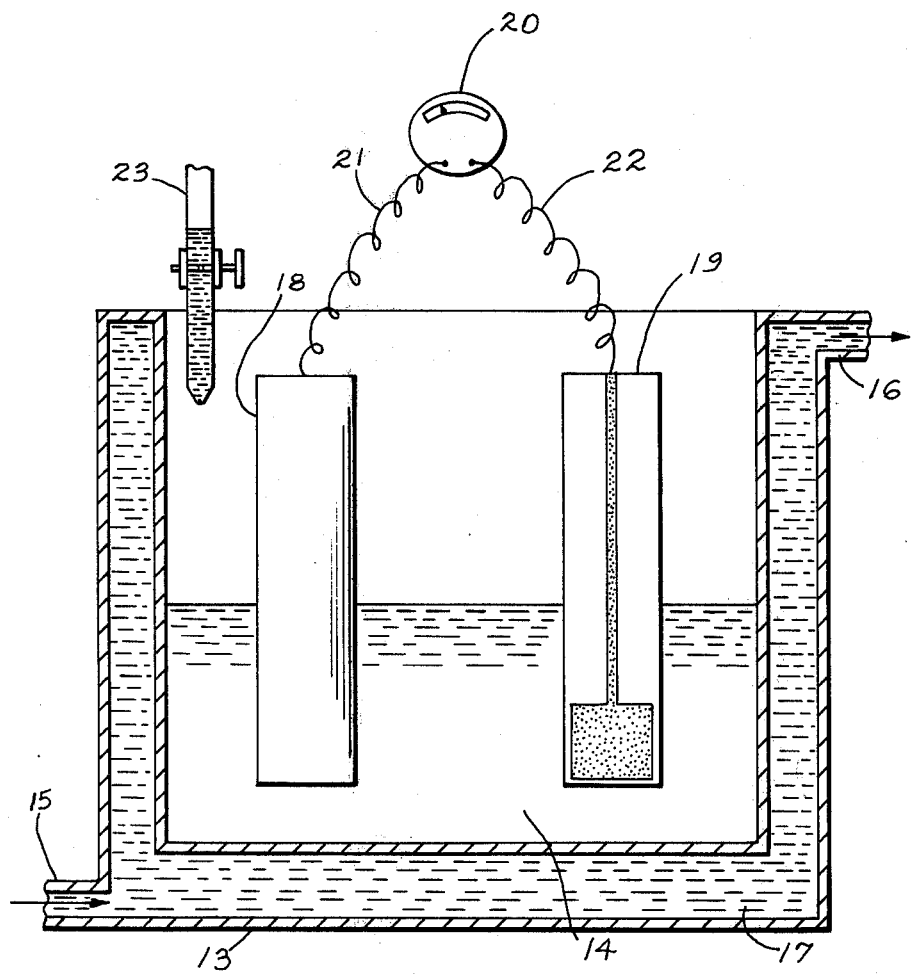
FIG. 2 is a semi-diagrammatic vertical sectional view of an electrochemical apparatus incorporating the solid sensor electrode of this invention which can be used for performing potentiometric titrations. A double-walled glass vessel 13 containing unknown solution 14 to be titrated is equipped with inlet 15 and outlet 16 through which are passed a thermostatically controlled fluid 17 which maintains the temperature of unknown solution 14 at a predetermined desired level. Reference electrode 18 and solid sensor electrode 19 are immersed in unknown solution 14 which also acts as an electrolyte for the two electrodes. A potential measuring device 20 is connected to reference electrode 18 by means of wire 21 and to solid sensor electrode 19 by means of wire 22. Buret 23 is used to titrate the unknown solution 14. As titrant is added from buret 23 to unknown solution 14 the potential between reference electrode 18 and solid sensor electrode 19 changes in a predetermined manner.

The titration of 100 ml. of $7.65 \times 10^{-3}$ M Fe(II) solution with 0.0956 M Ce(IV) was followed potentiometrically using the apparatus illustrated in FIG. 2. A Keithley Model 610B multi-range electrometer equipped with a Keithley Model 6107 electrode adapter was used as the potential measuring device 20. A saturated calomel electrode was used as reference electrode 18 and either a Beckman 39273 platinum inlay electrode, a platinum solid sensor electrode (as described in Example 4), a gold solid sensor electrode (as described in Example 3) or a palladium/gold solid sensor electrode (as described in Example 5) was used as electrode 19.

The Fe(II) solution was prepared by dissolving 0.3 g. Fe(NH$_4$)$_2$(SO$_4$)$_2$·6H$_2$O in 100 ml. of 1.0 M H$_2$SO$_4$ and the Ce(IV) solution was prepared by dissolving Ce(SO$_4$)$_2$·4H$_2$O in 1.0 M H$_2$SO$_4$.

The titrations were conducted in a 150 ml. cell consisting of a double-walled glass vessel with water thermostated at 30° ± 0.5° C. circulating in the space between the walls.

Figure 3:
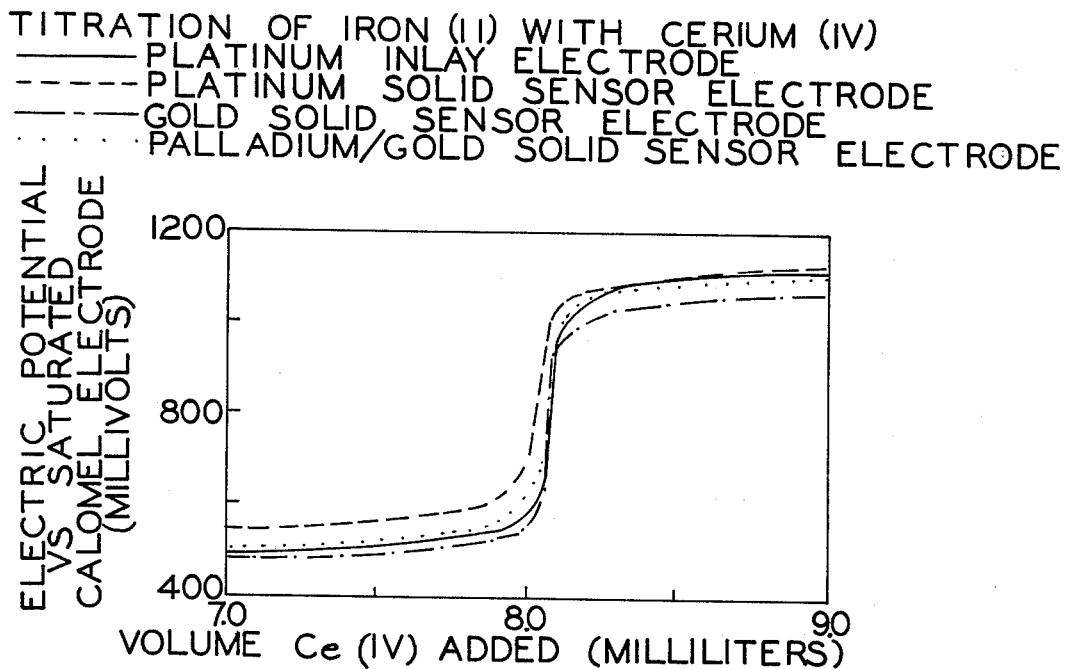
FIG. 3 and 4 are plots of electrical potential as recorded by potential measuring device 20 against the volume of titrant added which result in the typical S-shaped titration curves shown, from each curve the end point of the titration can be calculated and the concentration of unknown solution 14 determined.

The resulting titration curves are shown in FIG. 3. The end points calculated from the curves are shown in Table 6. The theoretical end point was calculated to be 8.00 ml.

TABLE 6

| Electrode | End point, ml. |
| --- | --- |
| Platinum inlay | 8.00 |
| Platinum sensor | 7.96 |
| Gold sensor | 7.99 |
| Palladium/gold sensor | 8.00 |

EXAMPLE 8

The titration of 80 ml. of 0.01 M NaCl with 0.0947 M AgNO$_3$ was followed potentiometrically using the apparatus of Example 7 except that the electrodes used were a saturated calomel electrode with a double junction containing 1 M KNO$_3$ and either a Beckman 39261 silver billet electrode or a silver solid sensor electrode (as described in Example 2) plated with silver chloride. The electrodes were plated by placing a pair of similar electrodes in saturated KCl solution, connecting one electrode to the positive pole of a 1½ v. dry cell and the other electrode to the negative pole thereof, reversing the current polarity to clean and recoat the desired electrode, and then disconnecting the electrodes from the dry cell.

Figure 4:
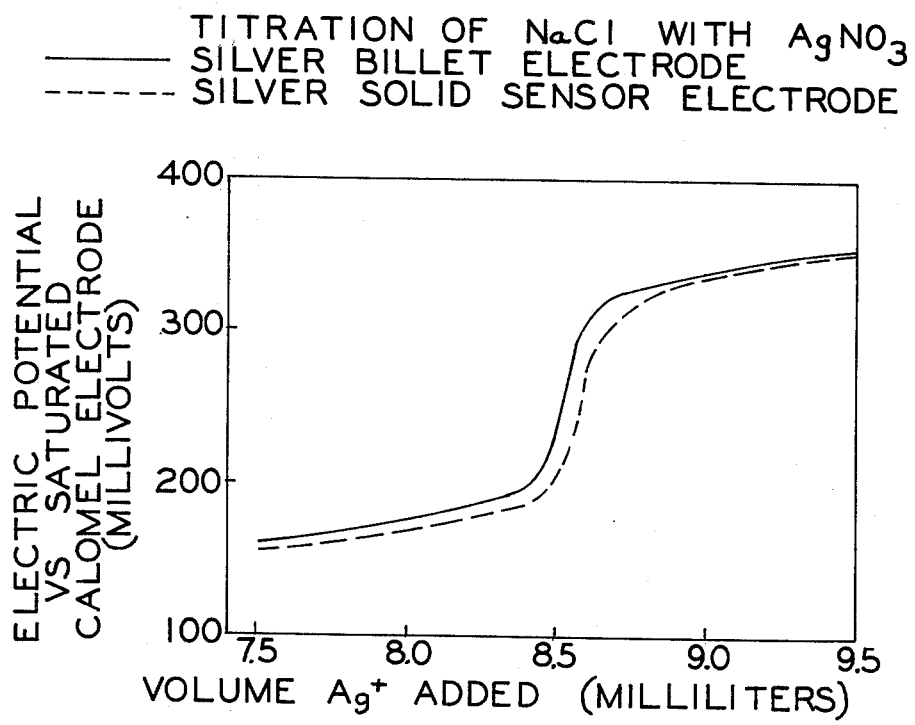

The resulting titration curves are shown in FIG. 4. The end points calculated from the curves are shown in Table 7. The theoretical end point was calculated to be 8.45 ml.

TABLE 7

| Electrode | End point, ml. |
| --- | --- |
| Silver billet | 8.43 |
| Silver sensor | 8.50 |

The solid sensor electrodes of this invention can be used in a large number of potentiometric titrations in addition to those exemplified above. For example, they can be used in the titration of As(III) with Br$_2$ or the titration of Br$^{31}$ with Ag(I). In addition the solid sensor electrodes can be used in other electrochemical measurements such as in polarographic determinations.

EXAMPLE 9

Cyclic polarograms of 1.0 × 10$^{-3}$ M K$_4$Fe(CN)$_6$ in 0.1 M phosphate buffer, pH 6.0 were obtained using a Heath Model EUA-19-2 polarograph module, Heath Model EUW-19A operational amplifier system and a Houston Instrument Model HR-97 X-Y recorder. A saturated calomel electrode was used as the reference electrode and a Beckman 39273 platinum inlay electrode was used as the counter electrode. Either a Beckman 39273 platinum inlay electrode having an area of approximately 0.2 cm.$^2$, a gold solid sensor electrode (as described in Example 3) having an area of approximately 1.0 cm.$^2$ or a palladium/gold solid sensor electrode (as described in Example 5) having an area of approximately 1.0 cm.$^2$ was used as the test electrode.

The electrodes were pretreated by immersing in a dichromate-sulfuric acid cleaning solution for several seconds and rinsing three times with doubly distilled water prior to immersion in the test solution.

A potential of −0.2 v. vs. the saturated calomel electrode (SCE) was then applied until the cathodic current decayed close to zero. Then the potential was moved to +0.05 v. vs. SCE until the current again decayed close to zero.

The cyclic polarograms were recorded in unstirred solutions at a sweep rate of 5 volts per minute using the double-walled thermostated vessel described in Example 7.

Figure 5A:
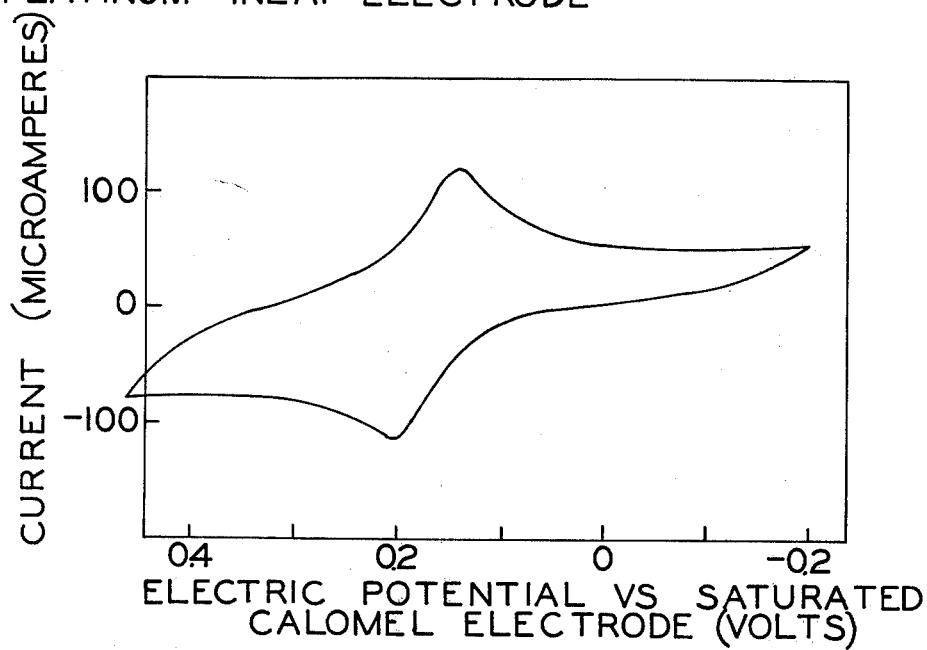
FIGS. 5A, 5B and 5C are cyclic polarograms for various electrodes as indicated.
Figure 5B:
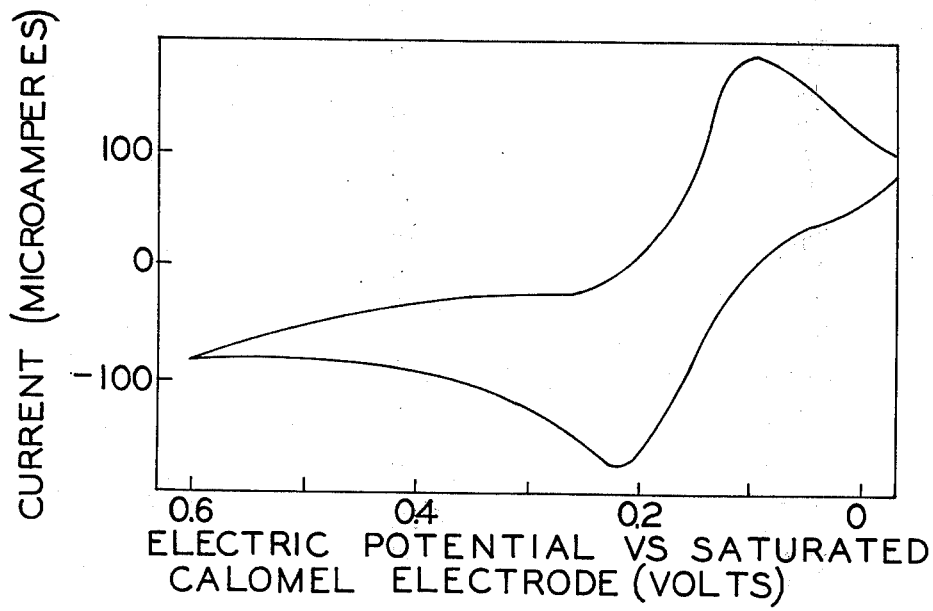
Figure 5C:
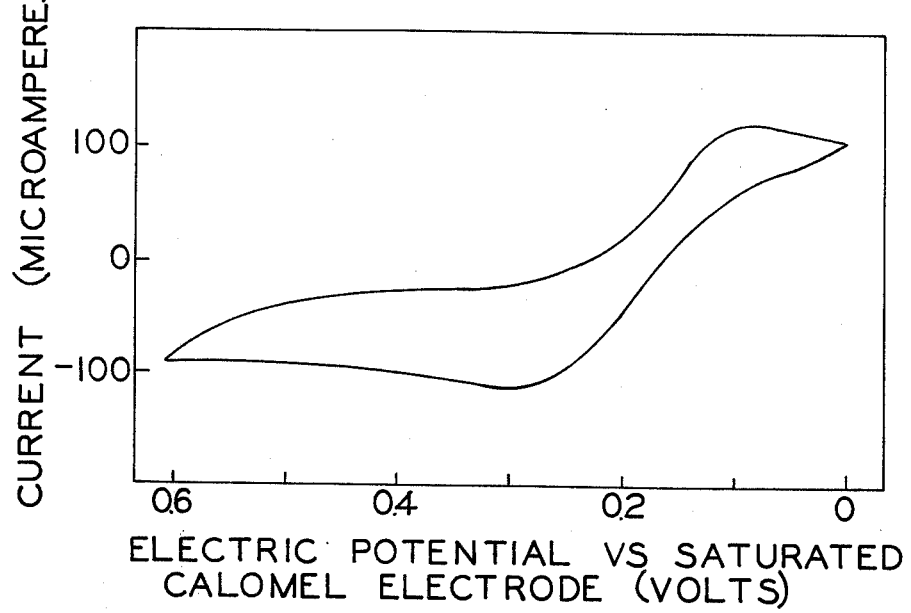

The resulting polarograms are shown in FIGS. 5A, 5B and 5C. The peak current/geometrical electrode area was about the same for the platinum inlay electrode and the palladium/gold solid sensor electrode approximately 85 micro-amperes per square centimeter. The value for the gold solid sensor electrode was about twice that of the others, approximately 185 micro-amperes per square centimeter.

In addition to the potentiometric and polarographic measurements illustrated above the solid sensor electrodes of this invention can be used in a variety of other electrochemical applications including amperometric, coulometric and other similar determinations.

We claim:

1. In a sensor electrode having a noble metal sensing surface adapted for direct contact with a test specimen, the improvement wherein said sensing surface comprises the composite, solid-state, fusion product of a mixture of noble metal powder and powdered glass, fused to an inert substrate.

2. An electrode according to claim 1 wherein said composite comprises about from 50% to 99% by weight of noble metal, the balance consisting of glass.

3. An electrode according to claim 1 wherein said noble metal is gold, silver, platinum, palladium or a mixture thereof.

4. An electrode according to claim 1 wherein said substrate is glass.

5. An electrode according to claim 1 wherein said substrate is a low alkali glass.

6. An electrode according to claim 1 wherein said substrate contains about 44.9% SIO$_2$, 19.0% Al$_2$O$_3$, 15.1% MgO and 21.0% CaO.

7. An electrode according to claim 1 wherein said substrate is a plastic material.

8. An electrode according to claim 1 wherein said substrate is alumina.

9. An electrode according to claim 1 wherein the glass present in said composite is a low alkali glass.

* * * * *